(12) United States Patent
Wiegerinck et al.

(10) Patent No.: US 8,801,627 B2
(45) Date of Patent: Aug. 12, 2014

(54) SAMPLER

(75) Inventors: Martinus Antonius Hermanus Maria Wiegerinck, Eindhoven (NL); Herman Jan Tijmen Coelingh Bennink, Driebergen (NL); Petrus Johannes Boerrigter, Apeldoorn (NL)

(73) Assignee: Pantarhei Bioscience B.V., Zeist (NL)

( * ) Notice: Subject to any disclaimer, the term of this patent is extended or adjusted under 35 U.S.C. 154(b) by 758 days.

(21) Appl. No.: 10/528,417

(22) PCT Filed: Sep. 23, 2004

(86) PCT No.: PCT/NL2004/000658
§ 371 (c)(1),
(2), (4) Date: Jul. 26, 2006

(87) PCT Pub. No.: WO2006/033569
PCT Pub. Date: Mar. 30, 2006

(65) Prior Publication Data
US 2006/0287610 A1    Dec. 21, 2006

(51) Int. Cl.
*A61B 10/00*      (2006.01)
*A61B 10/02*      (2006.01)
*A61B 17/34*      (2006.01)

(52) U.S. Cl.
CPC ......... *A61B 10/0283* (2013.01); *A61B 10/0096* (2013.01); *A61B 10/02* (2013.01); *A61B 10/0045* (2013.01); *A61B 10/0051* (2013.01); *A61B 2010/0074* (2013.01); *A61B 2017/3419* (2013.01)
USPC ........................................................ 600/563

(58) Field of Classification Search
CPC ............... A61B 10/0096; A61B 10/02; A61B 10/0283; A61B 17/43; A61B 2010/0074; A61B 2017/3419; A61B 10/0045; A61B 10/0051; A61M 25/1018

USPC .................... 600/563, 569–57, 578, 562, 35, 600/569–571; 604/1, 35, 218, 264, 540, 604/97.02
See application file for complete search history.

(56) References Cited

U.S. PATENT DOCUMENTS 3,540,432 A * 11/1970 Ayre .............................. 600/571
3,777,743 A    12/1973 Binard et al.
3,815,580 A *  6/1974 Oster ............................ 600/572
4,781,699 A * 11/1988 Suzuki et al. ................. 604/218

(Continued)

FOREIGN PATENT DOCUMENTS

EP    0947164 A1    10/1999
WO   0112072 A1    2/2001

OTHER PUBLICATIONS

Encyclopedia Britannica definition of mucus, 2009.*

*Primary Examiner* — Brian Szmal
(74) *Attorney, Agent, or Firm* — The Webb Law Firm

(57) ABSTRACT

Sampler for self-sampling of samples from a body cavity, such as cervical samples. Optimum accessibility of the cervix is achieved through the sampler comprising a rigid plastic tube which is rounded at the front side. During its introduction, the sampler can accurately be moved to the cervix. The sampler is surrounded by the vagina and can prevent leakage of flushing liquid, and it is possible to use a relatively small quantity of flushing liquid while producing a sample with a high concentration of cervical cells. It is possible to reach the sampling location in a simple and more accurate way which does not damage tissue. As a result of the tube simultaneously being designed as a cylinder for a plunger, it is possible, to flush the desired location with a solution using a cylinder-plunger and, to take the sample by drawing the plunger back.

20 Claims, 4 Drawing Sheets

(56) References Cited

U.S. PATENT DOCUMENTS

| | | |
|---|---|---|
| 5,045,058 A | 9/1991 | Demetrakopoulos |
| 6,022,326 A | 2/2000 | Tatum et al. |
| 6,071,231 A * | 6/2000 | Mendoza et al. ............... 600/35 |
| 7,207,951 B1 * | 4/2007 | Lurie et al. .................... 600/578 |

* cited by examiner

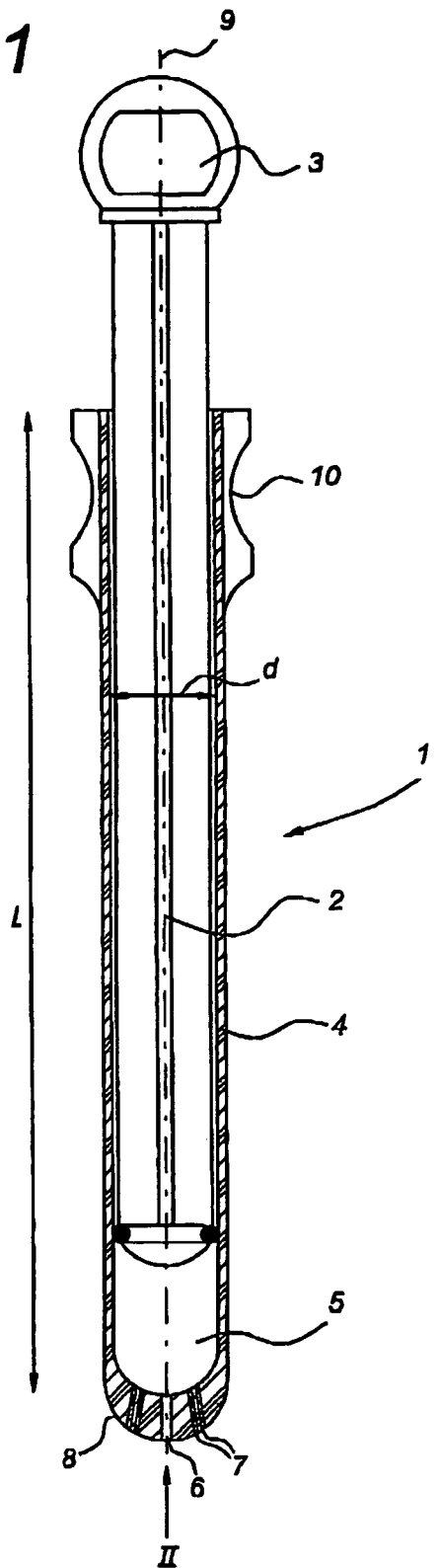
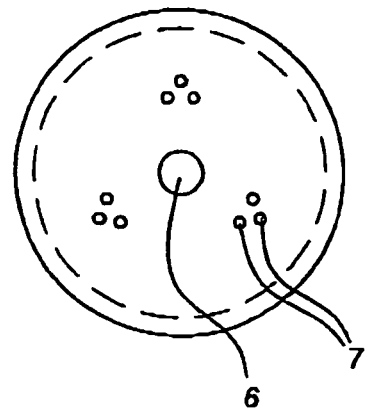

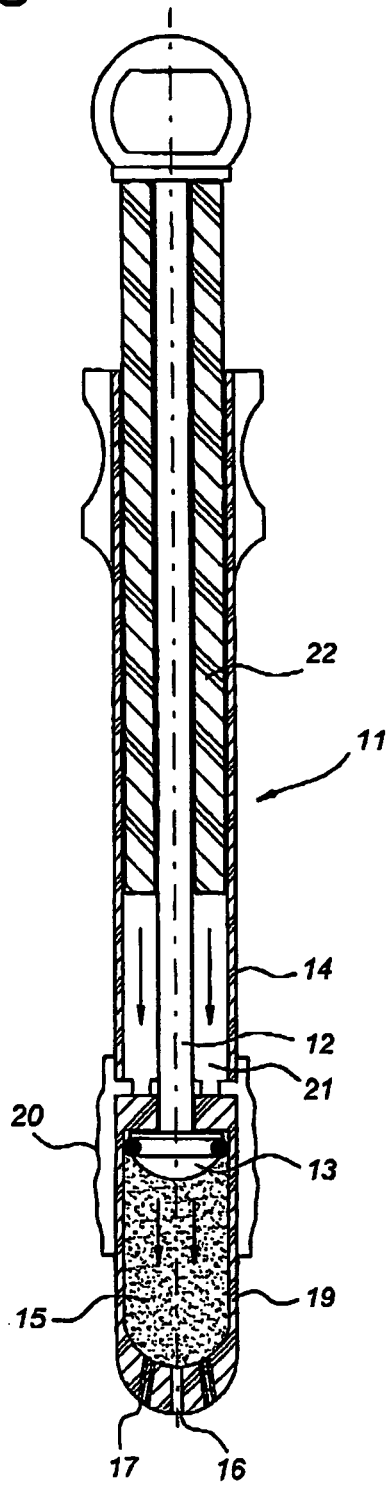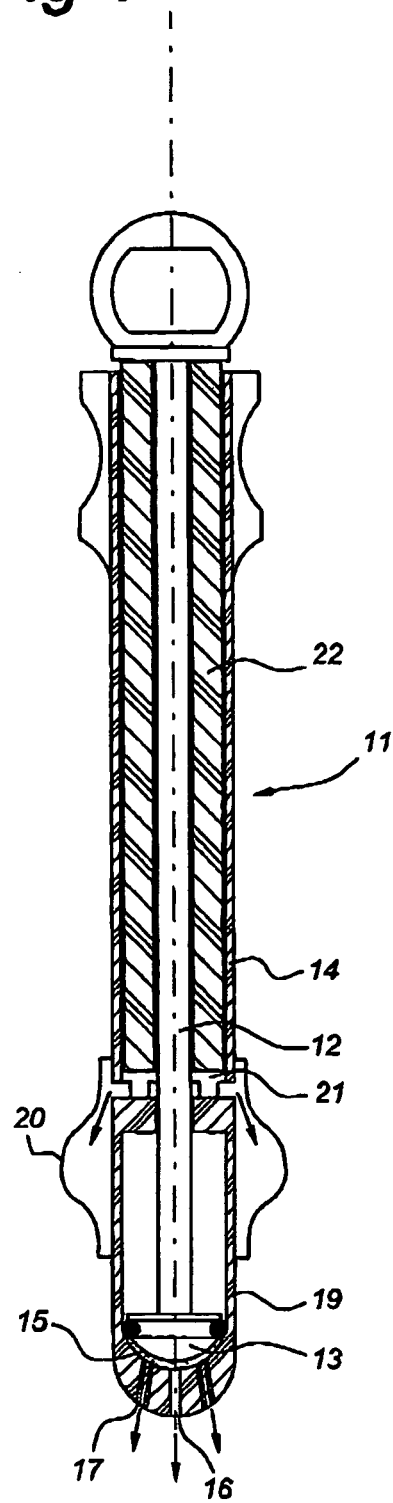

SAMPLER

DESCRITION OF RELATED ART

The present invention relates to a sampler.

BACKGROUND OF THE INVENTION

A sampler of this type is used, inter alia, to take samples such as from body cavities, and more particularly cervical samples. To counteract the disastrous consequences of cervical cancer, screening programs have been developed worldwide in which women undergo widespread examination. The usual method is to carry out a cervical smear (pap smear). However, is sampling has to be carried out by trained medical staff. A lot of women involved find this an unpleasant experience, and in addition it is inconvenient to have to visit the medical facility in question.

EP 0 947 164 A1 discloses a structure which enables trained physicians, eg. gynaecologists, to take a sample of the endometrium from the uterine cavity (detection of endometrial cancer). This device comprises an injection-like structure with a plunger-cylinder. Instead of the needle there is a tube which has to be introduced into the uterine cavity. A tube of this type has a diameter of approximately 3 mm and is relatively flexible. Openings for taking a sample are provided at the front side and laterally of the tube.

If it is correctly positioned, it has been found that a sampler of this type makes it possible to obtain good results with respect to obtaining endometrial tissue. A sampler of this type is not suitable to collect cervical cells (detection of cervical cancer or premalignant lesions). The design of the tube makes it impossible for women to use this device by themselves in order to collect a sample from the cervix or from the endometrium. At introduction into the vagina steering of the tube is relatively uncontrollable and there is no possibility to determine whether the end of the tube is at the correct location U.S. Pat. No. 3,777,743 discloses an endometrial sampler comprising a rigid hollow tube having a plurality of lateral sampling ports. The rigid tube has an outer diameter of about 0.07 inch (1 inch=2.54 cm) to be able to sample the uterine lining (endometrium). Although this tube might be better controllable due to its ratherly rigid nature accurate positioning is only possible by a skilled physician after exposing the cervix with a vaginal tenaculum because of its size. A sampler of this type is also only suitable to take a sample of the endometrium from the uterine cavity and is not suitable to collect cervical cells as is indicated in this disclosure.

U.S. Pat. No. 5,045,058 discloses a cleansing apparatus comprising a phallic-shaped solid soap material containing an antiseptic contained in a storage case which also can function as a syringe to rinse the vagina. The device allows rinsing when filled with fluid. The device is not suitable for collecting fluid from a body cavity such as the vagina. The device is difficult to handle when used for rinsing in case of self use due to numerous steps to take (i.e. fitting different parts together, filling the device with fluid) and missing a grip on the device for accurate positioning of the top of the device.

Until now little success has been achieved with women taking i.a. a cervical sample or cervical smear themselves, despite the fact that the desire for a device of this type has been expressed a number of times in the prior art

SUMMARY OF THE INVENTION

The object of the present invention is to provide an improved sampler which can be used by women themselves and gives a reliable sample.

In a sampler for taking a sample from a body cavity such as cervical samples, this object is achieved in that such sampler comprises a tubular means to be introduced in said cavity, the introduction end of which is cured to define a central sampling opening, storage means connected to said tubular means and vacuum means connected to said storage means and/or tubular means, said tubular means comprising a rigid tube having a diameter of at least 1 cm, and only at the curved introduction end a number of sampling openings is provided having a diameter of less than 5.

The considerable thickness of the sampling tube which is to be introduced compared to the prior art (from approximate 1 cm and preferably approximately 2 cm) makes it easier to feel for the user. The rounded end firstly pushes away adjoining parts of the cavity and secondly means that contact with the edge of the cavity is not painful. Since the tube is rigid, i.e. not flexible, the user can manipulate it accurately. The use of a substantially cylindrical tube means that when the latter is being introduced into a hollow cavity with a blind end, such as the vagina, of which the wall is formed by muscle tissue, an tight closure is formed between this wall and the tube, i.e., in the case of the vagina, a closure is created in its deepest part, where the cervix from which the sample is to be taken is located. Because of the relatively large diameter also position in such a blind end is optimised. The user can accurately feel the end of the tube without painful sensations. The length of the tube is at least approximately 15 cm. It comprises preferably one part but can comprise more parts.

Another problem with a further prior art device is that it is necessary to use a relatively large quantity of flushing liquid (15-50 ml is customary) to be certain that the desired flushing effect has been achieved, since the liquid flows back directly along the hose during flushing. Moreover, it is not certain that the sample will contain sufficient cells to obtain a useful measurement result. It is only possible to determine how accurately the tube was introduced on analysis in a laboratory.

The design of the present invention makes it possible both to introduce the flushing liquid and to take the sample. Since the cervix or other intended sampling location can be reached very accurately and a closure is formed in the manner described above, it is possible to make do with a very small quantity of flushing liquid (physiological saline). An example which can be mentioned for cervical sampling is 5 cc. This is lower by a factor of three than has hitherto been applied, with the result that the effect that solutions of this type might have on the environment in the cavity is greatly limited. The use of a small volume of fluid contributes to the comfort of the procedure for the user. Also, the sampling itself can be carried out with a greater degree of reliability in terms of the result achieved. After all, the smaller quantity of rinsing liquid means that it is possible to obtain a higher concentration of the sample. Since the sample actually enters in the protected environment of the interior of the tube, the risk of the sample being destroyed is greatly limited compared to the standard methods for taking a cervical smear. Consequently, in principle a smaller sample can suffice. Of course, it is necessary to take measures to protect the cells immediately after the sample has been taken. It has been found that the method of sampling described above is more comfortable for the women. After the sample has been sucked up, scarcely any moisture remains behind, with the result that no unpleasant backflow is observed after sampling. Moreover, the risk of delicate tissue being damaged is considerably limit. After all, the shaping of the sampling tube, in combination with the presence of several separate small openings, means that the risk of damage to, for example, the cervix and the vagina wall, is minimal. This contrasts with other designs which have bee proposed in the prior art. According to one possibility of the invention, the sampler itself is provided with sample containing means. However, it is now preferable for the sample to be transferred to a further container which has been filled with a preserving agent. Since a preserving agent of this type is often physiologically incompatible with the human body, measures have to be taken to prevent an agent of this type from being introduced into the body. The use of a separate container offers the best guarantee in this respect. Obviously, it is possible to arrange special designs in the sampler so that preserving agent is effectively prevented from moving into the human body in this way. If the sampler is designed as a cylinder-plunger, all types of locking means in combination with spring structures can be provided for this purpose.

Although the sampler has been described above on the basis of the sampling of the vaginal cavity, it should be understood that it is also suitable, if appropriate after being suitably modified, for sampling other cavities. It can also be used to introduce fluids into other cavities in the manner described above.

The rounding at the introduction end is designed in such a manner that the sampler can be introduced painlessly and easily by the user, unlike a flexible tube or sampling brushes or scrapers which are currently used to remove cells from the cervix for examination. The shape and size of the rounded introduction end are such that there is virtually no risk of damage to vaginal tissue or to the cervix.

The rounding at the introduction end of the tube is preferably designed in such a manner that the plane of the central sampling opening extends perpendicular to the centre line of the sampler.

To achieve optimum flushing, separate small openings may be present in the vicinity of the introduction end. These openings have preferably a diameter smaller than 5 mm and more particular about 2 mm. Also due to the presence of these small openings, the chance of the occurrence of uncontrolled vacuum force is minimal. This because upon insertion of the device into the cavity not all openings will be closed due to contact with the cavity wall and thus uncontrolled vacuum force will not be crated. Designing them as a one way opening according to a preferred embodiment of the invention, i.e. such that it is only possible for material to move out through them, allows central provision of sufficient suction for the cells which are to be sampled. This can be relised by providing a valve-like structure. However, it is also possible to choose the diameter of the opening so small that during the suction stoke the openings will be blocked by the tissue suction. Suction of this type can be achieved by, for example, drawing back a plunger in a cylinder. A return movement of this type after a flushing liquid has been introduced may either be carried out by hand or with the aid of a spring by unlocking a catch or the like. Further control of the under pressure applied by the device according to the invention can be obtained if the return movement of the plunger is defined for example through the presence of abutment means restricting the stroke thereof.

Tests have shown that the device according to the present invention allows the samples to be taken in a simple and reliable way. Of the users 98.5% classified the procedure as easy to perform by themselves with the help of a written instruction (manual). Users experienced fewer traumatic feelings and the quality of the diagnostic performance was considerably improved compared to the prior art, which improved subsequent conclusions in a laboratory considerably.

It will be understood that dispatch to the laboratory may take place in any way which is known in the prior art. If a separate container is used, this can be sent by post after it has been closed. Data provided by the person taking the sample can be applied to a container of this type. It has been found that a small quantity of sample is sufficient to obtain a representative result. In practice, one ml has proven sufficient.

In the case of designs in which the sample remains in the sampler, the sampler can be sent back by post or may be delivered to the point of issue or elsewhere.

To provide even more accurate sampling, according to an advantageous embodiment, a part which can be expanded outwards, such as a balloon part, may be present in the vicinity of the introduction end of the sampler. After the sampler has been introduced, this part can be inflated, so that the body cavity is closed up further, thereby eliminating the small risk of any of the flushing liquid leaking back. The method described above can be used, inter alia, for cytological examination of the cervix
    determination of HPV (human papilloma virus DNA) in cervical cells
    to detect Chlamydia (sexually transmittable disease)
    determination of gonorrhoea (sexually transmittable disease)
    carry out insemination (sperm partner, sperm donor)
    therapeutic flushing The invention also relates to a sampler assembly wherein said liquid containing means is filled with a flushing solution, more particular a physiological saline. In one embodiment, the liquid containing means has a volume of less than 10 cc.

The invention also relates to a kit comprising the sampler as described above as well as a closable container for containing said sample, said container being separate from said sampler.

The invention relates to a method for taking a sample from a body cavity, such as cervical samples, comprising introduction of a sampler tube into the entrance of said cavity, moving the tube in said cavity up to contact with the blind end of the cavity and taking a sample by suctioning material at the end of said sampler tube through an opening thereof wherein after inserting said sampler tube and before taking a sample a flushing solution is expelled from said sampler tube into said body cavity. More particular the flushing solution is expelled from a chamber inside said tube and said sample is introduced in said chamber. According to a further preferred embodiment after sampling a container is provided and the contents of the sampling tube is transferred with a container which is subsequently closed and shipped. The container can be provided with a preserving agent.

The invention will be explained in more detail below on the basis of exemplary embodiments illustrated in the drawing, in which:

BRIEF DESCRIPTION OF THE DRAWINGS

FIG. 1 shows a cross section through a first embodiment of the sampler according to the invention;

FIG. 2 shows a front view of the sampler shown in FIG. 1;

FIG. 3 shows part of a second sampler according to the invention in a first position;

FIG. 4 shows the illustration presented in FIG. 3 in a second (sampling) position;

DETAILED DESCRIPTION OF THE INVENTION

Figure 5:
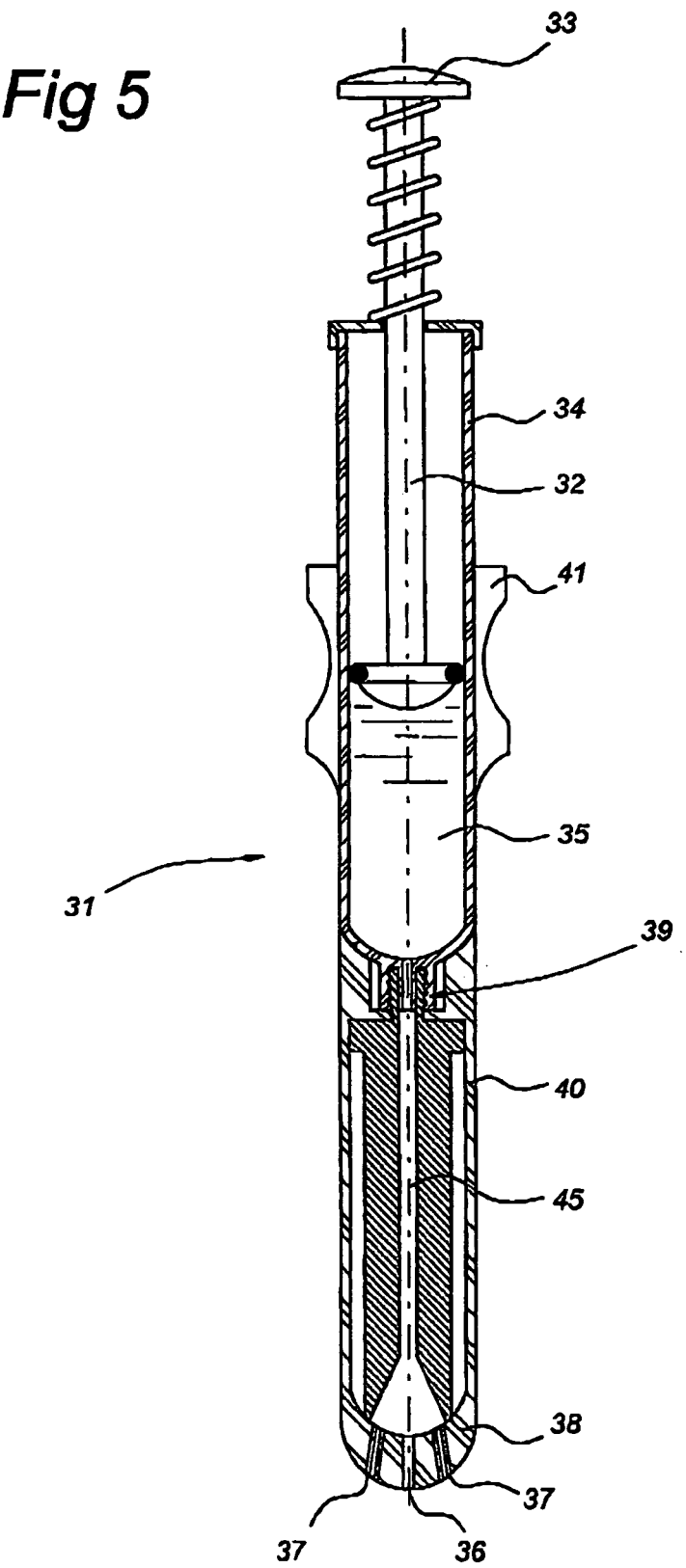
FIG. 5 diagrammatically depicts a further variant of the invention.

In FIG. 1, 1 denotes a sampler according to the invention. It comprises a plunger 2 which is arranged in a cylinder 4.

Plunger 2 can be moved with handle 3, which is preferably made from plastic. In the vicinity of the introduction end, cylinder 4 is provided with a sampling opening 6 and a number of spray openings 7 (cf. also FIG. 2). The introduction end is denoted by 8 and of rounded design. The rounding is gradual, in such a manner that the front surface, in the vicinity of sampling opening 6, is substantially perpendicular to the centre line 9. It will be understood that the sampler according to the present invention may also be rounded in other ways. However, all this must be such that, during introduction into body cavities, any obstacles can easily be pushed aside and the user can gain an accurate feeling as to the position of the device without causing any injury.

The length of the cylinder is denoted by L and is preferably more than 15 cm, in particular approximately 16 cm. The diameter is denoted by d and is at least approximately 1 cm.

Figure 6:
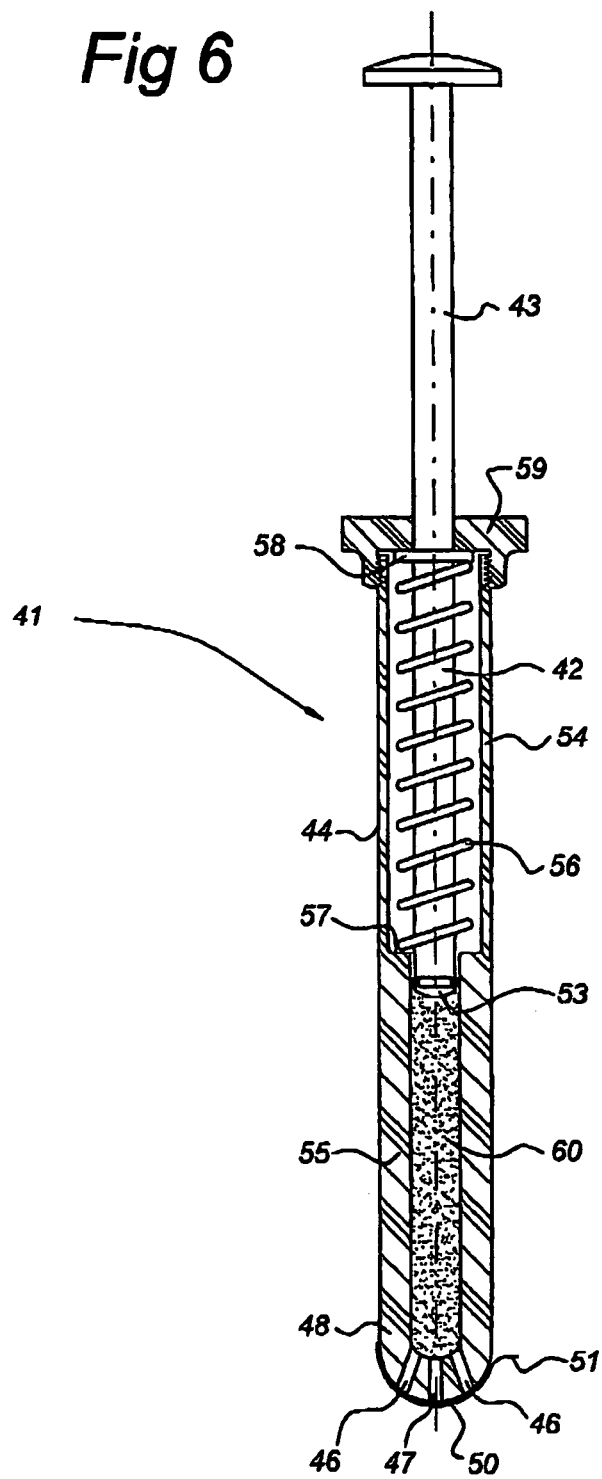
FIG. 6 shows a further embodiment of the invention.

The sampler described functions in the following way:

In the start position shown in FIG. 1, the space 5 for the plunger is filled with physiological saline. If a sample is to be taken from the cervical cavity, the device is introduced with the aid of the cylinder grip 10. Because the cylinder 4 comprises a rigid plastic tube, highly sensitive and accurate positioning is possible. The user can accurately move the rounded end 8 to the vicinity of the cervix. The rounded end 8 enables the user to accurately detect contact with the cervix. At that moment, plunger handle 3 has to be moved towards cylinder grip 10, so that the flushing liquid 5 is forced outwards. Then, plunger handle 3 has to be moved back with respect to cylinder grip 10. This movement may be relatively small. According to an advantageous embodiment, at most approximately 5 cc of physiological saline is induced, and it is sufficient to take a sample of approximately 1 cc. To limit the return movement, there may be blocking and/or locking means (as shown in FIGS. 3, 4 and 6). After the sample has been taken, it can be transferred to a separate container which is filled with a fixative fluid. It is also conceivable to use designs in which the sample is stored in a protected form in space 5. This can be achieved, for example, by screwing on a auxiliary device which contains a fricative fluid. A suitable design makes it possible for the up-and-down movement of the plunger to be carried out just once, so that it is ensured that fluid is not unintentionally sucked up and then returned to the user's body.

FIGS. 3 and 4 show a further variant of the invention, and more particularly only the bottom end of this valiant. This is denoted overall by 11. The plunger tube or cylinder is denoted by 14, while the plunger itself comprises a plunger rod 12 and a plunger end 13. This plunger end 13 moves to and fro in a separate capsule 19 which in turn is provided at its end with a central outlet opening 16 and flushing openings 17. In this case too, volume 15 is filled with physiological saline. A flexible ring 20 is arranged between capsule 19 and plunger tube 14.

During the introduction movement, the capsule 19 will be pressed onto the plunger tube 14. Since the plunger rod 12 is not actuated, there will be no change in pressure in chamber 21. After it has been introduced in a suitable way, the physiological saline is expelled from the space 15. This is achieved by moving the plunger rod 12.

Contrary to the design described above, here is a sleeve 22 which is connected to the plunger rod and can be displaced in chamber 21. It is activated by the plunger grip. Activating it causes the volume in chamber 21 to decrease and the flexible part 20 to swell, as shown in FIG. 4. As a result, the relevant cavity can be closed effectively.

FIG. 5 shows a further embodiment of the present invention. This is denoted overall by 31 and comprises a plunger 32 and handle 33. The plunger 32 moves in a cylinder 34 which is provided with a ribbed structure 41 which can be gripped by hand. In front of the plunger there is a fluid compartment 35.

Unlike in the embodiment described above, the tube of the sampler 31 is composed of two parts. In addition to the cylinder part 34 described above, there is also a tube part 40 which can be coupled to it. This has the same external diameter as cylinder 34. On the inner side there is a passage 45 with a small diameter, while in the vicinity of the free end 38, as in the embodiment described above, there ate openings 36 and 37, the openings 37 being used to discharge flushing liquid. The tubes 34 and 40 are connected with the aid of any connection which is known in the prior art, in this case a screw thread connection which is denoted overall by 39. It will be understood that it is also possible for bayonet, clip-action, snap-action and similar connections to be used instead of a screw thread connection 39 of this type. The split design of the sampler in accordance with the embodiment shown in FIG. 5 enables part 34 and 40 to be sterilized in a simple way, so that it is easier to take account of the demands imposed with regard to storage and shelf life of irrigation liquid.

In FIG. 6 a further embodiment of the invention is known. The sampler is referred to by 41 and comprises a tube 44 having an introduction end 48 with a central sampling opening 47 and sideholes 46. These openings are closed with a sealing strip 50 having an engagement tab 51 for peeling of lip 50. Plunger 42 can be moved with handle 43. The plunger end 53 is in a non-activated condition in the position shown in FIG. 6. Cylinder 44 comprises an upper part 54 having a relative large diameter and a lower part 55 having a small diameter. The small diameter part is sized to receive plunger end 53 in sealing engagement. Upper part 54 is designed to receive both the plunger 42 and a spring 56 provided there around. On the one hand this spring supports on step 57 and on the other hand at a projection 58 on top of the plunger 42. This projection also acts as an abutment against the end closure 59 of tube 44. In the position shown in FIG. 6 below the plunger end 53 a volume 60 is defined which preferably contains a physiological saline of which the volume is accurately known.

For operating this device the user removes strip 50 by engaging tab 51. Subsequently, the device is inserted in the related cavity. The depth of the insertion of the device is individualised by stopping further insertion once resistance is felt at reaching the deepest part of the related cavity. Alternatively through markings on the outer side of tube 44 the user can exactly determine how deep the device is inserted. After adequate insertion grip 43 is activated to move plunger 42 in downward direction expelling the physiological saline from volume 60. After reaching the lowest point of plunger 42 by simple releasing plunger handle 43, because of the presence of spring 56, plunger end 53 makes a return movement with a predetermined stroke and consequently a predetermined volume of the sample is taken.

It will be understood that the end position of the plunger end 53 as well as the return movement of the plunger can be realised in any other way.

The person skilled in the art, on reading the above, will immediately arrive at other variants which are obvious and lie within the scope of the appended claims.

EXAMPLE 1

A study has been performed to test the device of the present invention on its reliability and practicability of self-sampling of cervix cells in 110 women in the home situation with regard to HPV detection in comparison with a classical pap smear.

All these women received the self-sampler at home including a written instruction. They also visited the clinic for making a pap smear by a physician.

The HPV rest of material take by women using the device of the present invention at home and by the trained physician using the classical pap smear method is comparable.

In addition, 98.5% of the users of the device of the present invention classified the procedure as easy to perform by themselves with the help of the written instruction.

The invention claimed is:

1. A sampler for taking a sample from a body cavity comprising a tubular means adapted to be introduced in said cavity, a storage means connected to said tubular means and a vacuum means connected to said storage means and/or said tubular means; said tubular means comprising a rigid tube having a smooth outer surface and a diameter of at least 1 cm and a curved introduction end, wherein said rigid tube in operation provides a closure in the body cavity for a flushing solution when expelled; said sampler further comprising a number of sampling openings wherein said sample opening are positioned only at the curved introduction end of said tubular means, wherein said number of sampling openings comprises a central opening having a diameter of less than 5 mm; said sampler further comprising a liquid containing means and a pump means to expel said flushing solution from said liquid containing means through said curved introduction end of said rigid tube.

2. The sampler according to claim 1, wherein said vacuum means comprise said pump means.

3. The sampler according to claim 1, wherein said storage means comprise said liquid containing means.

4. The sampler according to claim 1, wherein said liquid containing means have a volume of less than 10 cc.

5. The sampler according to claim 1, wherein said vacuum means comprise a plunger-cylinder.

6. The sampler according to claim 5, wherein said rigid tube comprises said cylinder.

7. The sampler according to claim 1, comprising a sealing means for said openings.

8. The sampler according to claim 1, wherein said vacuum means comprises a plunger in said tubular means, wherein abutment means are provided to define relative movement of said plunger and said tubular means.

9. A kit, comprising the sampler according to claim 1 and a closable container for containing said sample, said container being separate from said sampler.

10. The sampler according to claim 1 wherein the flushing solution is saline.

11. A sampler assembly, comprising a sampler for taking a sample from a body cavity comprising a tubular means adapted to be introduced in said cavity, a storage means connected to said tubular means and a vacuum means connected to said storage means and/or tubular means, said tubular means comprising a rigid tube having a smooth outer surface and diameter of at least 1 cm and a curved introduction end, said sampler further comprising a number of sampling openings only at said curved introduction end, wherein said number of sampling openings comprises a central opening having a diameter of less than 5 mm wherein said sample openings are positioned only at the curved introduction end of said tubular means; said sampler further comprising a liquid containing means and a pump means to expel a flushing solution from said liquid containing means through said curved introduction end of said rigid tube, said rigid tube in operation provides a closure in the body cavity for said flushing solution when expelled.

12. The sampler assembly according to claim 11, wherein said flushing solution comprises physiological saline.

13. A kit, comprising the sampler assembly according to claim 11, and a closable container for containing said sample, said container being separate from said sampler.

14. The sampler assembly according to claim 11 wherein the flushing solution is saline.

15. A method for taking a sample from a body cavity comprising introducing a sampler tube into the entrance of said cavity, said sampler tube comprising a tubular means adapted to be introduced in said cavity, a storage means connected to said tubular means and a vacuum means connected to said storage means and/or said tubular means, said tubular means comprising a rigid tube having a smooth outer surface and a diameter of at least 1 cm and a curved introduction end; said sampler tube further comprising a number of sampling openings wherein said sample openings are positioned only at the curved introduction end of said tubular means, wherein said number of sampling openings comprises a central opening having a diameter of less than 5 mm, said sampler further comprising a liquid containing means and a pump means to expel a flushing solution from said liquid containing means through said curved introduction end of said rigid tube, said rigid tube in operation provides a closure in the body cavity for a flushing solution when expelled; moving said sampler tube in said cavity up to contact with a blind end of the cavity; expelling said flushing solution into said body cavity; and taking said sample by suctioning said sample at said curved introduction end of said sampler tube through said number of sampling openings.

16. The method according to claim 15, wherein said flushing solution is expelled from a chamber inside said tube and said sample is introduced in said chamber.

17. The method according to claim 15, wherein said flushing solution comprises a physiological saline solution.

18. The method according to claim 15 further comprising transferring said sample to a container.

19. The method according to claim 18, wherein said container is provided with a preserving agent.

20. The method according to claim 15 wherein the flushing solution is saline.

* * * * *